United States Patent [19]

Hayashi

[11] Patent Number: 4,669,471

[45] Date of Patent: Jun. 2, 1987

[54] FORCEPS DEVICE FOR USE IN AN ENDOSCOPE

[75] Inventor: Shigeo Hayashi, Tokyo, Japan

[73] Assignee: Olympus Optical Co., Ltd., Tokyo, Japan

[21] Appl. No.: 669,314

[22] Filed: Nov. 7, 1984

[30] Foreign Application Priority Data

Nov. 10, 1983 [JP] Japan .................................. 58-211517
Apr. 19, 1984 [JP] Japan .................................. 59-79189

[51] Int. Cl.⁴ .............................................. A61B 17/28
[52] U.S. Cl. ..................................... 128/321; 228/139; 128/305
[58] Field of Search .......... 227/DIG. 1; 219/121 LD, 219/121 L, 121 ED; 228/139; 128/321, 305; 411/171, 501-507

[56] References Cited

U.S. PATENT DOCUMENTS

| | | | |
|---|---|---|---|
| 3,895,636 | 7/1975 | Schmidt | 128/321 |
| 3,911,766 | 10/1975 | Fridolph et al. | 128/321 |
| 4,038,987 | 8/1977 | Komiya | 128/321 |
| 4,290,545 | 9/1981 | Whitney | 228/139 |
| 4,531,044 | 7/1985 | Chang | 219/121 L |

Primary Examiner—Gene Mancene
Assistant Examiner—John G. Weiss
Attorney, Agent, or Firm—Robert E. Burns; Emmanuel J. Lobato; Bruce L. Adams

[57] ABSTRACT

A forceps device for use in an endoscope is described. The device comprises a pair of forceps cups capable of closing and opening, a link member, an operating wire, and a flexible tube. Pivot pins for connecting the forceps cups to the link, the link to the operating wire and the forceps cups to the connecting portion of the flexible tube are fused or welded to corresponding portion of components with the use of laser welding process.

12 Claims, 15 Drawing Figures (PRIOR. ART)

(PRIOR. ART)

(PRIOR. ART)

FORCEPS DEVICE FOR USE IN AN ENDOSCOPE

BACKGROUND OF THE INVENTION

The present invention relates to a forceps device for use in an endoscope.

Such a forceps device is shown in FIG. 1 and comprises a forceps or clamp member which is so operated that it is inserted into an entrance aperture 3 provided at an operating portion 2 of an endoscope 1 and projected from an exit aperture 7 provided at an end portion 6 of the endoscope 1 through at least one channel (not shown) formed in a connecting portion 4 and a bend portion 5 of the endoscope, thereby performing desired object.

As shown in FIGS. 1 and 2, the forceps device comprises a flexible tube 10 capable of being inserted into the channel of the endoscope 1, an operating portion 11 provided at a base portion 10a of the tube 10, a forceps head 12 provided at a tip portion 10b of the tube 10, and a pair of forceps cups 8 forming the forceps and provided to the head 12 in a manner capable of opening and closing.

Each forceps cup 8 has a connecting portion 8a and a connecting extension 13 which is connected through a link 14 to a wire coupling 16 connected to a tip 15a of an operating wire 15 which is extended through the tube 10, and hence coupled to the operating wire 15.

The operating wire 15 has a base portion (not shown) which is connected to an operating column 17 of the operating portion 11.

When the column 17 moves backward and forward the wire 15 can be moved backward and forward in the tube 10 and thus the pair of forceps cups 8 can be closed and opened about a connecting pin 19 provided to a cover 18 having a slitted opening of the head 12 as a fulcrum.

The pair of forceps cups 8 of the device 9 are so constructed that the extension 13 provided to the connecting portion 8a of cups 8 is connected to the link 14 by first connecting pin, the link 14 is connected to the operating wire 15 through the coupling member 16, and the connecting portions 8a of the cups 8 are connected to each other and to the cover 18 having slitted opening which is provided to the head 12 in a manner capable of closing and opening.

Connecting means of these components is described hereinafter with respect to FIGS. 3a and 3b as well as FIGS. 4 and 5. As shown in FIG. 3a, a butting portion 13a of the extension 13 is butted to the link 14, an aperture 13b of the extension 13 is registered to an aperture 14a of the link 14, and a connecting pin 20 is inserted into and fitted in the registered apertures 13b and 14a.

The pin 20 has a length longer than that $l_1$ equal to a sum of thickness of the extension 13 and the link 14 so that a head portion 20a of the pin 20 and the side surface of the link 14 become coplanar after fitting the pin 20 in the apertures 13b and 14a and a tip portion 20b of the pin 20 is projected from the side surface of the extension 13.

The projected tip portion 20b of the pin 20 is, then, caulked to cause plastic deformation resulting in a formation of caulked portion 20c so that the pin 20 is held in the apertures 13b and 14a and thus the extension 13 and the link 14 are rotatably connected to each other by the pin 20 (refer to FIG. 3b).

As shown in FIG. 4, then, both links 14 are butted to a butting portion 16b of the coupling member 16, an aperture 14b of the link 14 is registered to an aperture 16a of the coupling member 16, and a connecting pin 21 is inserted into and fitted in the apertures 14b and 16a, thereby connecting links 14 to the coupling member 16 and thus the operating wire 15.

The pin 21 has a length longer than that $l_2$ equal to a sum of thickness of the coupling member 16 and both links 14 so that a head portion 21a of the pin 21 and the side surface of one link 14 become coplanar and a tip portion of the pin 21 is projected from the side surface of the other link 14 after fitting the pin 21 in the apertures 14b and 16a. The projected tip portion of the pin 21 is caulked to cause plastic deformation resulting in a formation of caulked portion 21c so that the pin 21 is held in the apertures 14b and 16a and thus the coupling member 16 and both links 14 are rotatably connected to each other by the pin 21.

As shown in FIG. 5, in order to connect both forceps cups 8 to the cover 18 having a slitted opening of the forceps head 12, the connecting portions 8a of both cups 8 are inserted in the slitted opening of the cover 18 and thus both links 14 connected to the portions 8a and the coupling member 16 connected to both links 14 are also inserted in the slitted opening.

Then, apertures 8b of both connecting portions 8a are registered to apertures 18a of the cover 18 and a connecting pin 22 is inserted in the registered apertures 8b and 18a.

The pin 22 has also a length longer than that $l_3$ equal to an outer diameter of the cover 18 so that a head portion 22a of the pin 22 and the side surface of the cover 18 become coplanar and a tip portion of the pin 22 is projected from the side surface of the cover 18 after fitting the pin 22 in the apertures 8b and 18a. The projected tip portion of the pin 22 is caulked to cause plastic deformation resulting in a formation of caulked portion 22c so that the pin 22 is held in the apertures 8b and 18a and thus both forceps cups 8 and the cover 18 are rotatably connected to each other by the pin 22.

As described above, the connection of respective components are performed by the caulked portions 20c, 21c and 22c of connecting pins 20, 21 and 22 so that caulking operation becomes complicated. In addition thereto it is necesssary to file respective caulked portions 20c, 21c and 22c during working in order to make these portions 20c, 21c and 22c coplanar with surfaces of the extension 13, the link 14 and the cover 18, respectively. It is also necessary to adjust respective components and variation of quality for respective workers since operating conditions of respective connecting portions are dependent on connecting conditions of respective pins 20, 21 and 22.

SUMMARY OF THE INVENTION

It is an object of the present invention to overcome the above described disadvantages of conventional forceps device.

It is another object of the present invention to provide a forceps device for use in an endoscope in which connecting work of respective components due to caulking work is made easy and operating conditions of respective connecting portions are not dependent on connecting conditions of pins.

According to the present invention there is provided a forceps device for use in an endoscope comprising a pair of forceps cups capable of closing and opening each having a connecting portion and an extension portion therefrom, a link member connected to the extension by a first connection pin, an operating wire having a connecting portion connected to the link by a second connection pin, a flexible tube having a connecting portion connected to the connecting portions of the cups by a third connection pin, the third pin also connecting the connecting portions of the cups to each other, and the operating wire being extended through the flexible tube, a first pivot pin connecting the extension to the link, a second pivot pin connecting the link to the connecting portion of the operating wire, and a third pivot pin connecting portions to each other and connecting them to the connecting portion of the flexible tube.

Respective pivot pins comprise a pin body having same diameter over its length, a head portion having a diameter larger than that of the pin body, and a tip portion having a diameter equal to that of the pin body. The tip portion of the pivot pin is fused by laser beam to connect it to the corresponding material of the forceps cup extension, the link and the flexible tube connecting portion. The head portion of the pivot pin is fused by laser beam to connect it to the corresponding material of the forceps cup extension, the link and the flexible tube connecting portion. The fused portion(s) of the pivot pin is formed by a laser spot having a diameter larger than that of the end portion to be fused and/or a plurality of laser spots each having a diameter smaller than that of the end portion to be fused.

BRIEF DESCRIPTION OF THE DRAWINGS

These and other features and advantages of the present invention will become readily apparent from the following detailed description of one embodiment of the present invention, particularly when taken in connection with the accompanying drawings wherein like reference numerals designate like or functionally equivalent parts throughout, and wherein.

DESCRIPTION OF THE PREFERRED EMBODIMENT

Figure 1:
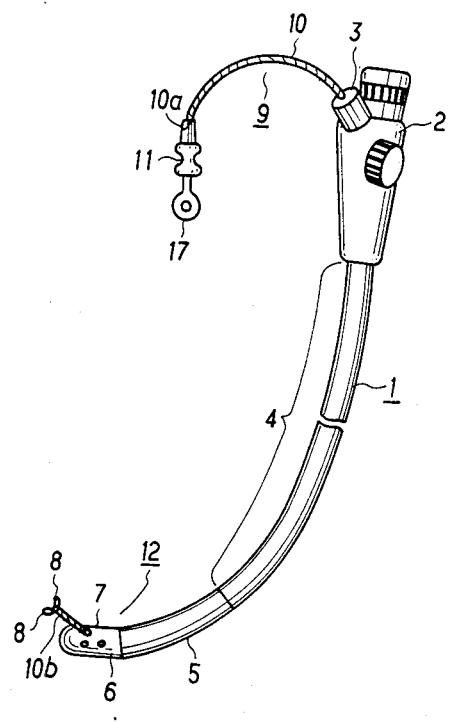
FIG. 1 is a perspective view showing a conventional endoscope and a forceps device for use therein.
Figure 2:
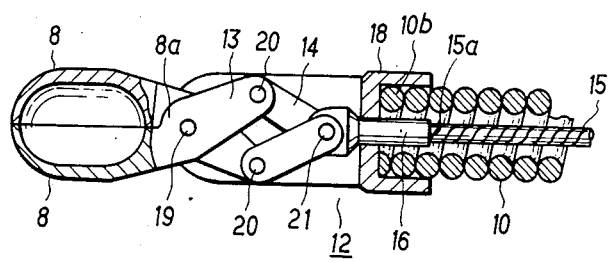
FIG. 2 is a partially sectional view illustrating the forceps device shown in Fig. 1.

Referring now to the drawings, there are shown several embodiments of a forceps device for use in an endoscope according to the present invention.

Figure 6:
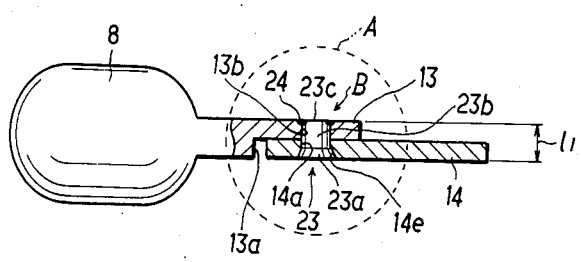
FIGS. 6 to 8 are elevational views partly in section showing first, second and third embodiments of respective pivot portions of pivot pins used in forceps device according to the present invention.

FIG. 6 shows one embodiment of a forceps or clamp member for use in the forceps device in which a connection of the connecting extension 13 of the forceps cup 8 to the link 14 is shown. This embodiment is quite the same as that shown in FIG. 3, except that use is made of a pivot pin 23 instead of the connecting pin 20, and the fusing tip portion 23c of the pin 23 is welded by laser beam to form a welded portion 24 thereby connecting the pivot pin 23 to the extension 13.

The pivot pin 23 has a length of a value $l_1$ at most equal to a sum of thickness of the extension 13 of the cup 8 and the link 14 butted thereto, and is inserted in the pivoting apertures 13b and 14a in such a manner that the head portion 23a of the pin body 23b is fitted in a fitting aperture 14e of the link 14 having a diameter larger than that of the aperture 14a and the fusing end 23c of the pin body 23b and the surface of the extension 13 become at most coplanar.

Figure 9:
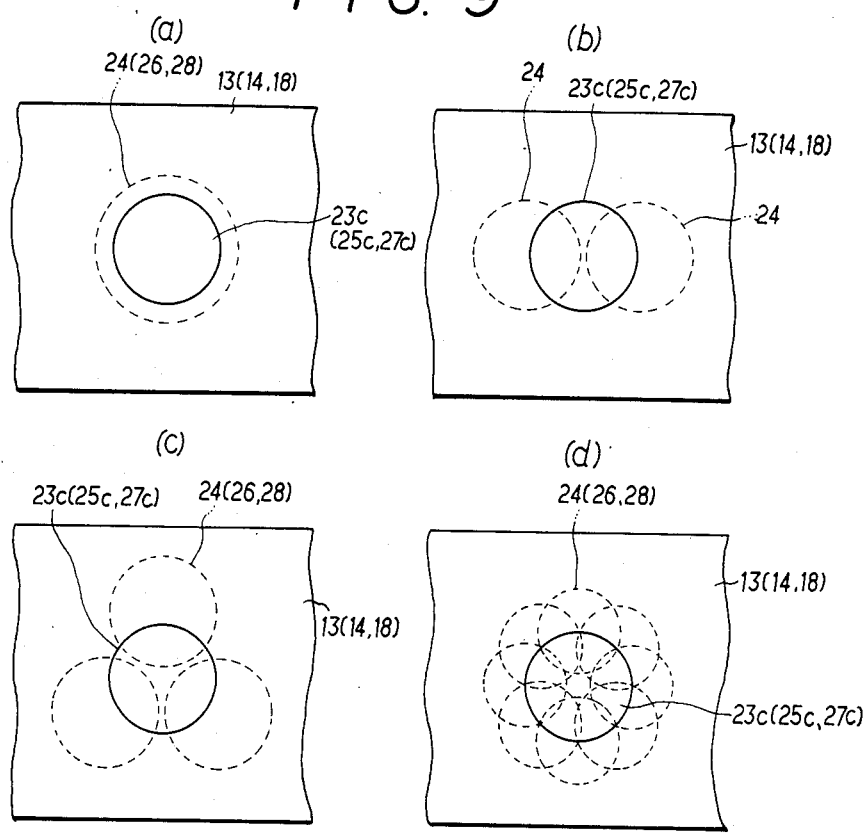
FIGS. 9a to 9d are enlarged plan views illustrating welded portions by laser beam at tip portion of pivot pins shown in FIGS. 6 to 8.

The fusing end portion 23c of the pivot pin 23 is connected to the extension 13 of the cup 8 by fusing the portion 23c along the opening periphery of the pivoting aperture 13b with the use of laser welding work, resulting in formation of the fused portion 24. The fused portion 24 formed by the laser spot is shown in FIG. 9 as enlarged. FIG. 9a shows the fused portion 24 with only one laser spot having a larger diameter than that of the fusing end portion 23c. FIG. 9b shows the fused portion 24 with two laser spots each having same diameter as that of the end portion 23c. FIGS. 9c and 9d show the fused portion 24 with three and multiple laser spots, respectively. These laser beams may be projected on the end portion to be fused in the directions parallel to the axis of aperture or inclined thereto. The laser such as a YAG laser, carbonic acid gas laser or a ruby laser may be used for the laser welding work.

Figure 3:
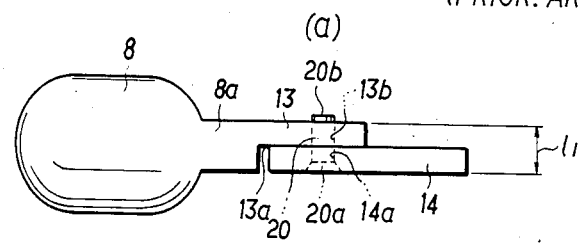
FIGS. 3a, 3b, 4 and 5 are elevational views partly in section illustrating respective connecting portions of elements used in the conventional forceps device.
Figure 4:
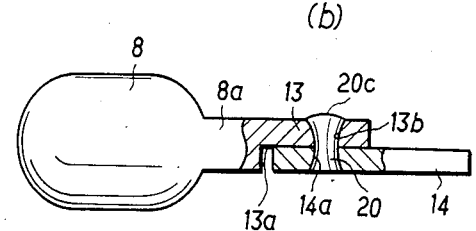
Figure 5:
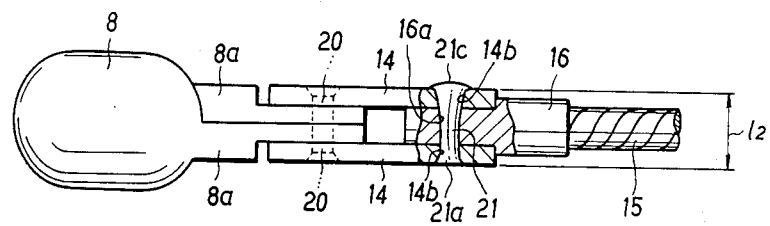
Figure 5:
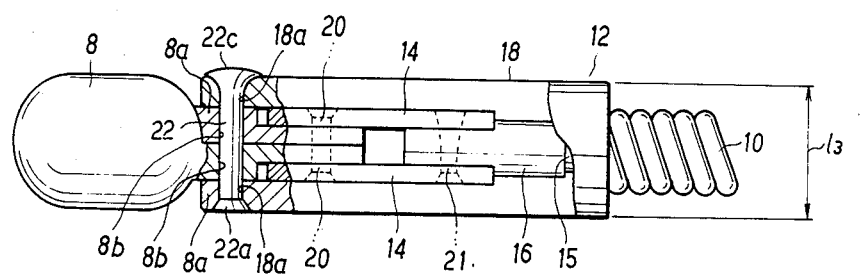

In FIG. 6 corresponding parts are designated by the same reference numerals as in FIG. 3 and its explanation is omitted.

Figure 7:
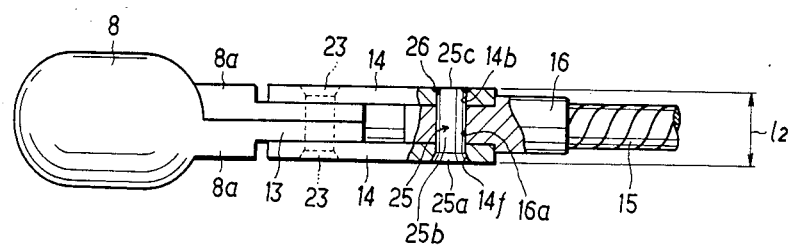

FIG. 7 shows the embodiment of connecting the link 14 connected to the extension 13 of the cup 8 to the operating wire 15 by the coupling member 16.

In this embodiment a pivot pin 25 having a length of a value $l_2$ at most equal to a sum of thickness of the coupling member 16 and both links 14 butted thereto is inserted in the pivoting apertures 14b of the links 14 and the pivoting aperture 16a of the coupling member 16 and then a fusing end portion 25c of the pivot pin 25 is connected to one of the links 14 by fusing the end portion 25c along the opening periphery of the pivoting aperture 14b with the use of laser welding work resulting in a formation of a fused portion 26 so that the pivot pin 25 is held in the apertures 14b and 16a.

The welding means may be carried out in the same manner as FIGS. 9a to 9d so that its explanation is omitted. In this embodiment a head portion 25a of the pivot pin 25 is just fitted in a fitting aperture 14f provided at the opening periphery of the aperture 14b and having a larger diameter than the fitting aperture 14b.

Figure 8:
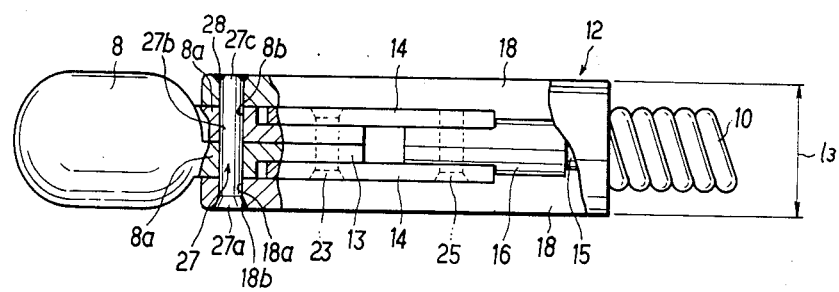

FIG. 8 shows the embodiment of connecting the forceps cup 8 to the forceps head 12 as a connecting portion of the flexible tube 10.

In this embodiment the connecting portions 8a of the cups 8 are inserted in the slitted opening of the cover 18 and a pivot pin 27 is inserted in pivoting apertures 18a of the cover 18 and pivoting apertures 8b of the connecting portions 8a of both cups 8.

The pivot pin 27 has a length of a value $l_3$ at most equal to a diameter of the cover 18 having the slitted opening and a fusing end portion 27c of the pivot pin 27 is fused to the side surface of the cover 18 with the use of laser welding work resulting in formation of a fused portion 28 so that the pivot pin 27 may be held in the apertures 18a and 8b and thus both cups 8 may be pivoted to the cover 18 by the pin 27. In this embodiment a head portion 27a of the pin 27 is just fitted in a fitting aperture 18b provided at the opening periphery of the pivoting aperture 18a and having a larger diameter than the aperture 18a.

Now, means for forming the fused portion 24 is further explained with reference to FIG. 10 which is an enlarged figure of a portion A shown in FIG. 6.

Figure 10:
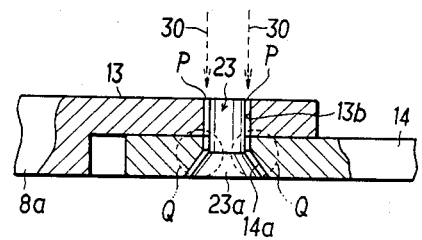
FIGS. 10 and 11 are elevational views partly in section illustrating connection means of respective pivot portions of the pivot pin shown in FIG. 6.

The laser welding work for the fusing end portion 23c of the pivot pin 23 may be carried out by projecting a laser beam 30 shown in FIG. 10 by dotted arrow onto the end portion 23c.

In this case, if the laser beam is projected on the fusing end portion 23c in the direction parallel to the axis of the aperture 13b, this laser beam is introduced in a gap P formed between the pivoting aperture 13b of the extension 13 and the pivoting aperture 14a of the link 14 and thus the portion Q is also welded so that the extension 13 of the cup 8 is welded to the link 14. At the portion B (refer to FIG. 6), also, the pivot pin 23 is welded to the extension 13 of the cup 8 so that the pivot pin 23, the forceps cup 8 and the link 14 are integrally welded to each other resulting in an incapability of action.

Figure 11:
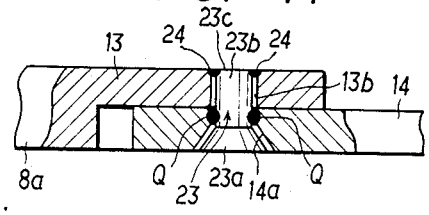

Such a fused condition among the pin 23, the cap 8 and the link 14 is shown in FIG. 11. In order to overcome such a disadvantage the gaps formed between the pin 23 and the pivoting aperture 13b of the cup 8 and between the pin 23 and the pivoting aperture 14a of the link 14 must be made as small as possible. However, the limit of present working allowance is in the order of ±0.01 mm so that the gap becomes 0.02 mm. When laser power is small the laser beam introduced in the gap does not weld the corresponding portion, and the welding strength at the desired portion B becomes weak.

That is, in order to fuse or weld the fusing end portion 23c of the pin 23 and the pivoting aperture 13b of the cup extension 13 a certian welding strength is desired so that it is necessary to increase laser power of the laser beam 30 used for welding work of the fused portions 24, 26 and 28. This increase of laser beam includes the problem shown in FIG. 11.

Such a problem may be resolved by modifications shown in FIGS. 12 to 15.

Figure 12:
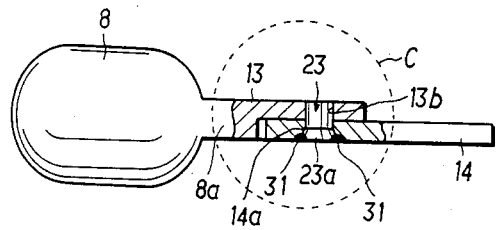
FIGS. 12 to 14 are elevational views partly in section illustrating first and second modifications of respective pivot portions of pivot pins shown in FIGS. 6 to 8.

In the modification shown in FIG. 12 the head portion 23a of the pivot pin 23 is utilized as a fusing end portion instead of the fusing end portion 23c shown in FIG. 6. That is, the pin 23 is connected to the link 14 by welding the fusing head portion 23a having larger diameter than the pin body 23b with the use of laser beam resulting in a formation of a fused portion 31 so that the pin 23 may be held in the aperture 13b and thus the pivoting end portion 23c of the pin 23 may be pivotably provied to the extension 13 of the cup 8. Other portion of the construction shown in FIG. 12 is the same as that shown in FIG. 6 so that its explanation is omitted.

Figure 13:
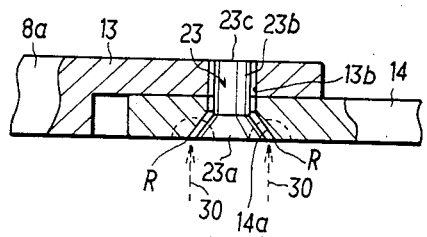

In this modification, as shown in FIG. 13, the head portion having large diameter can prevent the laser beam 30 from being introduced in the pivoting aperture 13b through the pivoting aperture 14a so that the welding or fusing is carried out only near the portion R shown in FIG. 13 by dotted line and thus the above problem may be resolved.

Figure 15:
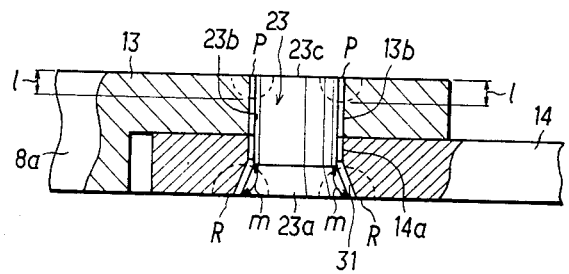
FIG. 15 is an enlarged plan view comparing and explaining connection means of respective pivot portions of pivot pins shown in FIGS. 4 and 12.

FIG. 15 illustrates a comparison of the fused portion 31 shown in FIGS. 12 and 13 with the fused portion 24 shown in FIGS. 6 and 10. Provided that fusion of both portions 24 and 31 is carried out by utilizing same laser power, if the gap and the material of components are made same, the same fused depth is obtained in the fused portions 24 and 31, but a length l at the boundary portion P in the fused portion 24 is smaller than a length m at the boundary portion R in the fused portion 31 so that the welding strength of the portion 31 may be increased.

Figure 14:
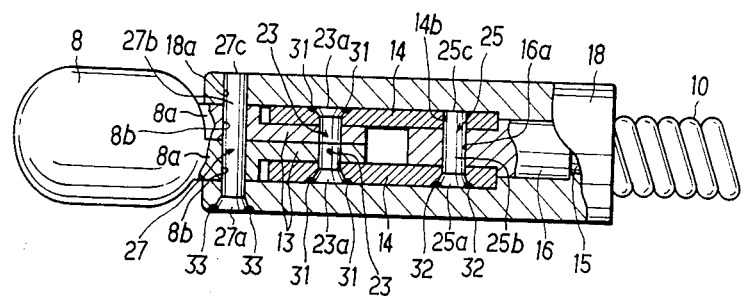

In the modification shown in FIG. 14 the head portion 25a of the pivot pin 25 is utilized as a fusing end portion instead of the fusing end portion 25c shown in FIG. 7 and the head portion 27a of the pivot pin 27 is utilized as a fusing end portion instead of the fusing end portion 27c shown in FIG. 8. Other portion of the construction shown in FIG. 14 is the same as those shown in FIGS. 7 and 8 so that its explanation is omitted.

In the above described embodiment when one end of the pivot pin 27 is fused to the pivoting aperture 18a of the cover 18 and the other end of the pivot pin 27 is not fused therto if the gap between the pivoting aperture 18a and the pivot pin 27 at the other end side the pivot pin 27 becomes flexible during operation of the forceps cup 8, so that the guide surface between the cover 18 and the link 14 becomes slidable. This results in non smooth operation of the cup 8.

Figure 16:
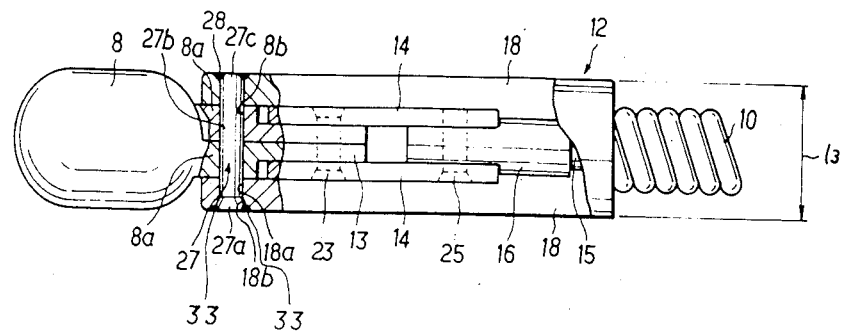
Figure 17:
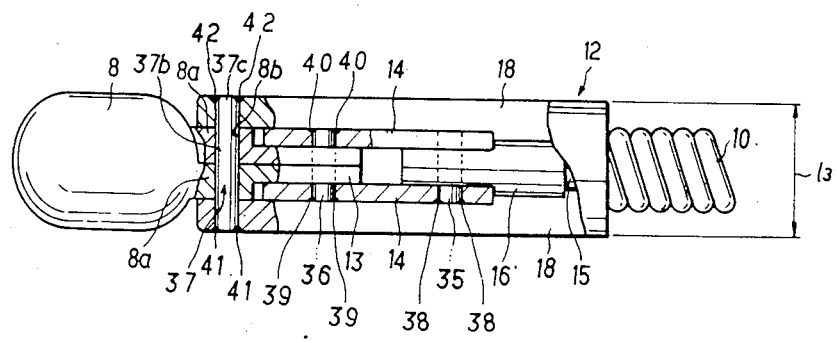

Such a problem may be resolved by modifications shown in FIGS. 16 and 17.

In the modification shown in FIG. 16 both end portions of the pivot pin 27 are fused to the corresponding material of the cover 18 to prevent a play of the pin 27. That is, the head portion 27a of the pin 27 is also fused to the cover 18 therby forming a fused portion 33 so that operation of the forceps cup 8 can be made smooth.

In the modification shown in FIG. 17, pivot pins 35,36,37 each having the same diameter over its length is used as the pivot pin 25,23 and 27. In this case pivot pin 37 is fused at both ends to the corresponding mateials of the cover 18 thereby forming fused portions 41 and 42. The pivot pins 35 and 36 are fused at its one end to the corresponding materials of the link 14 therby forming fused portions 38,39 and 40, respectively.

According to the present invention following advantageous effects may be obtained.

The proficiency for laser welding work is not necessary rather than caulking work so that the laser welding work may be standardized and variation of quality for worker may be reduced resulting in an increase of yield. The number of working steps, also, may be reduced as compared with conventional working steps such as caulking process or filing step. The forceps device may be smoothly moved because of no deformation of connection pin due to caulking process.

The present invention is not limited to the above described embodiments, but various modifications and alternations are possible. The other welding source may be utilized instead of laser beam source. The present invention may be applied to other type of forceps, such as a bioptic forceps or a scissor forceps or the like for use in the endoscope.

What is claimed is:

1. In an endoscope having a forceps device thereon the combination of a flexible tube having fixed on an end thereof a generally cylindrical cover which at an outer end is slitted diametrically to provide spaced branches, an operating wire movable lengthwise in said tube and having fixed on an end thereof a connector having a flat portion disposed between said branches of said slitted cover, a pair of forceps cups having pivot portions disposed between end portions of said branches of slitted cover and operating arm portions extending beyond said pivot portions and disposed between said branches of said slitted cover, a first pivot pin extending through aligned holes of uniform size in said pivot portions of said forceps cups and end portions of said branches of said slitted cover, said first pivot pin having a length of a value at most equal to the sum of the thickness of said forceps cup pivot portions and the thickness of said end portions of said branches of said slitted cover whereby ends of said first pivot pin do not project beyond outer surfaces of said branches, a first laser weld fusing at least one end of said first pivot pin to the respective branch of said slitted cover, a pair of links for connecting said operating arms of said forcep cups respectively with said connector on the end of said operating wire, a second pivot pin extending through aligned holes of uniform size in a first end of each of said links and an end of the operating arm of the respective forceps cup, each of said second pivot pins having a length of a value at most equal to the sum of the thickness of said link and the thickness of the operating arm of the respective forceps cup, a second laser weld fusing an end of said second pivot pin to one of said links being disposed on opposite sides of said flat portion of said connector, a third pivot pin extending through aligned holes of uniform size in said second ends of said links and said flat portion of said connector, said third pivot pin having a length of a value most equal to the sum of the thickness of said links and said flat portion of said connector and a third laser weld fusing an end portion of said third pivot pin to at least one of said links.

2. In an endoscope, a combination according to claim 1, in which said first pivot pin has at one end a head countersunk flush with an exterior surface of one of said branches of said cover and has at an opposite end a laser weld fusing said opposite end to the other of said branches of said cover.

3. In an endoscope, a combination according to claim 2 in which said laser weld fusing said opposite end of said first pivot pin to the other of said branches of said cover has an area larger than the area of said opposite end of said first pivot pin.

4. In an endoscope, a combination according to claim 2, in which said laser weld fusing said opposite end of said first pivot pin to the other of said branches of said cover comprises a plurality of weld area each smaller than the area of said opposite end of said first pivot pin.

5. In an endoscope, a combination according to claim 1, in which said second pivot pin has at one end a head countersunk flush with an outer surface of said link and has at an opposite end a laser weld fusing said opposite end to said operating arm of the respective forceps cup.

6. In an endoscope, a combination according to claim 1, in which said third pivot pin has at one end a countersunk head flush with an outer surface of one of said links and has at an opposite end a laser weld fusing said opposite end to the other of said links.

7. In an endoscope, a combination according to claim 1, in which said first pivot pin has at one end a head countersunk flush with an outer surface of one of said branches of said cover and a laser weld fusing said head to said branch of said cover.

8. In an endoscope, the combination according to claim 1, in which said second pivot pin has at one end a head countersunk flush with an outer surface of said link and a laser weld fusing said head to said link.

9. In an endoscope, the combination according to claim 1, in which said third pivot pin has at one end a head flush with an outer surface of one of said links and a laser weld fusing said head to said link.

10. In an endoscope, the combination according to claim 1, in which said first pivot pin is of uniform diameter throughout its length and has at least one end a laser weld fusing said end to a branch of said cover.

11. In an endoscope, the combination according to claim 1, in which said second pivot pin is of uniform diameter throughout its length and has at one end a laser weld fusing said pin to the respective one of said links.

12. In an endoscope, the combination according to claim 1, in which said third pivot pin is of uniform diameter throughout its length and has at one end a laser weld fusing said pin to the respective one of said links.

* * * * *